United States Patent
Hicks et al.

(10) Patent No.: US 6,668,183 B2
(45) Date of Patent: Dec. 23, 2003

(54) DIODE DETECTION CIRCUIT

(75) Inventors: Christopher Anthony Hicks, Boulder, CO (US); Mark A. Norris, Louisville, CO (US); Matti Veli Tapani Huiku, Espoo (FI); Scott James Charles Light, Boulder, CO (US)

(73) Assignee: Datex-Ohmeda, Inc., Madison, WI (US)

( * ) Notice: Subject to any disclaimer, the term of this patent is extended or adjusted under 35 U.S.C. 154(b) by 0 days.

(21) Appl. No.: 09/953,138

(22) Filed: Sep. 11, 2001

(65) Prior Publication Data

US 2003/0050545 A1 Mar. 13, 2003

(51) Int. Cl.$^7$ .................................................. A61B 5/00
(52) U.S. Cl. ...................... 600/331; 600/322; 600/323
(58) Field of Search ................. 600/310, 322, 600/323, 331, 500–507

(56) References Cited

U.S. PATENT DOCUMENTS

| | | |
|---|---|---|
| 5,287,853 A | 2/1994 | Vester et al. |
| 5,818,985 A | 10/1998 | Merchant et al. |
| 5,924,979 A | 7/1999 | Swedlow et al. |
| 6,023,541 A | 2/2000 | Merchant et al. |
| 6,351,658 B1 * | 2/2002 | Middleman et al. ........ 600/323 |

FOREIGN PATENT DOCUMENTS

WO        WO 00/18291        4/2000

* cited by examiner

Primary Examiner—Eric F. Winakur
Assistant Examiner—David J. McCrosky
(74) Attorney, Agent, or Firm—Marsh Fischmann & Breyfogle LLP (57) ABSTRACT

A photoplethysmographic system and method is provided to identify compatible sensors to monitors and/or for determining sensor attributes. The improved system includes a signal generation means for providing an interrogation signal, an identifying means coupled between a first and second sensor terminal operable to produce multiple outputs upon application of the interrogation signal in two modes of operation, and a processor to interpret the outputs. When the interrogation signal is applied to a sensor terminal in a first mode, a first output is obtained. Upon applying the same interrogation signal to the sensor terminal in a second mode, a second output is obtained. The first and second outputs may then be utilized by the processor comprising, for example, a photoplethysmographic monitor to yield enhanced sensor information. The disclosed method may be carried out utilizing the inventive photoplethysmographic system.

55 Claims, 4 Drawing Sheets

DIODE DETECTION CIRCUIT

FIELD OF THE INVENTION

The present invention relates to the field of photoplethysmography and, more specifically, to an improved system and method for determining sensor attributes. The invention is particularly apt for use in pulse oximetry applications to identify compatible sensors and/or otherwise to provide for the transfer of calibration and of other information between sensors and other system components.

BACKGROUND OF THE INVENTION

In the field of photoplethysmography light signals corresponding with two or more different centered wavelengths may be employed to non-invasively determine various blood analyte concentrations. For example, blood oxygen saturation ($SpO_2$) levels of a patient's arterial blood may be monitored in pulse oximeters systems by measuring the absorption of red and infrared light signals. The measured absorption data allows for the determination of the relative concentration of reduced hemoglobin and oxyhemoglobin and, therefore, $SpO_2$ levels, since reduced hemoglobin absorbs more light than oxyhemoglobin in the red band and oxyhemoglobin absorbs more light than reduced hemoglobin in the infrared band, and since the absorption relationships of the two analytes in the red and infrared bands are known. See e.g., U.S. Pat. Nos. 5,934,277 and 5,842,979.

Pulse oximeters systems typically comprise a disposable or reusable sensor that is releasably attached to a given patient's appendage (e.g., finger, ear lobe or the nasal septum) for a given patient monitoring procedure and include at least one red light source and one infrared light source. The light sources are focused though a patient's tissue and the unabsorbed light that passes through is measured to determine blood analyte concentrations.

As may be appreciated, in order to accurately compute blood analyte concentrations utilizing a given sensor, it is important that information regarding the sensor be known; for example, the center wavelengths of the light sources employed. A number of approaches have been developed for identifying sensor attributes to pulse oximeter monitors. By way of primary example, many sensors contain an electrical component having a characteristic(s) that may be measured by a pulse oximeter monitor when the sensor is interconnected thereto. Once the characteristic(s) is known, the monitor may determine what center wavelengths correspond with the sensor light sources, for example, by using a stored look-up table or correlation function. In turn, an appropriate calibration value can be utilized in determining blood analyte concentrations. Generally, the information in a stored look-up table or utilized to formulate a correlation function is based on data that corresponds with sensors originating from a known source. Such sources tend to approved by the monitor manufacturers and provide sensors and corresponding data that has been determined and verified through actual clinical use such that the sensors may be used with a high level of confidence. Increasingly, however, sensors are being offered for use with pulse oximeter monitors from additional sources which may, for example, utilize the same or similar identifying means as sensors from known sources while not necessarily utilizing light sources that have center wavelengths as the sensors from the known sources, thereby presenting potential difficulties in assuring accurate performance of the monitor/sensor combinations.

SUMMARY OF THE INVENTION

In light of the foregoing, a primary objective of the present invention is to provide a further improved approach for obtaining photoplethysmographic sensor information.

A related objective of the present invention is to provide for increased photoplethysmographic sensor information in a manner that does not increase sensor complexity.

Yet a further objective of the present invention is to provide for the communication of photoplethysmographic sensor information in a manner that facilitates enhanced reliability.

One or more of the above objectives and additional advantages are indeed realized by the present invention, wherein the disclosed photoplethysmographic system and method provides for the obtainment of at least one data value from a photoplethysmographic sensor in a two-mode process. In one aspect a photoplethysmographic system is provided that comprises: a signal generation means, a sensor identifying means and a processing means. More particularly, the signal generation means is able to provide at least one interrogation signal in two distinct modes of operation to the sensor identifying means. The sensor identifying means is operable to receive at least a first interrogation signal in two distinct modes of operation, wherein the interrogation signal is initially applied with a first polarity and then applied with an opposite polarity. The sensor identifying means is further operable to produce at least one output value for each mode of operation. The outputs produced by the sensor identifying means in response to the application of the two-mode interrogation signal may then be used by the processing means to determine sensor data.

By way of example, such sensor data may serve to identify a given sensor to a pulse oximetry monitor, wherein the monitor is enabled/disabled or otherwise calibrated for operation with the interconnected sensor. As will be appreciated, in conventional applications of the invention the signal generation means and processing means may be located at a pulse oximeter monitor, while the sensor identifying means may be located at a given cable interconnected thereto.

The signal generation means may further comprise a means for establishing the first and second modes of operation, wherein the interrogation signal may be applied in two distinct modes to a terminal of the sensor identifying means. For example, in the first mode, the establishing means may provide an interrogation signal to a sensor terminal with an initial polarity, while in a second mode the same interrogation signal may be applied to the same sensor terminal with an opposite polarity. The establishing means may be configured such that it automatically applies the interrogation signal in the two modes of operation when a sensor is attached to a pulse oximeter monitor. In one embodiment, the establishing means may comprise a power supply, an electrical storage means and a switching means. More particularly, the power supply may be operable to both provide an initial polarity to the sensor terminal and to provide power to charge the electrical storage means. For example, a power supply, such as a voltage divider, may supply a steady voltage to charge an electrical storage means and provide an initial interrogation signal with a steady state voltage.

With regard to the electrical storage means, an electrical potential may be stored from the power supply that may be selectively released by the switching means to change the system, for a predetermined time, from the first mode of operation to the second mode of operation. Releasing the stored electrical potential may cause the electrical operation in the system to be altered from a steady state operation to a transient condition. As will be appreciated, if the sensor identifying means is electrically connected to the signal generation means when the electrical operation is altered, the interrogation signal as applied to the sensor identifying means may also be altered, allowing for a second output reading to be taken during this altered state. For example, by selectively grounding a stored electrical potential, where the storage means is a charged capacitor, may cause an electrical imbalance in the signal generating system while the capacitor discharges. While discharging, the capacitor may pull electrical voltage from all electrically attached components, thus reversing the current flow and the polarity of the voltage as seen in the attached components. Typically, a processor will operate the switching means to selectively discharge the electrical storage means and change the system from the first mode of operation to the second mode of operation.

With regard to the sensor identifying means, one or more electrical components may be advantageously connected between a first and a second sensor terminal to produce output values in response to interrogation signals. The electrical components may be arranged in a manner such that the application of a single interrogation signal in two modes of operation (e.g., positive polarity and negative polarity) will produce two different output values. For example, an identifying means may comprise a simple resistor and a diode connected in parallel between the two sensor terminals; by applying a known voltage across the terminals such that the diode is reverse-biased and by measuring the resulting voltage drop, the size of the resistor can be determined. By correlating the voltage drop and/or the resistor size with predetermined sensor data tables, characteristics of the currently attached sensor can be determined. By reversing the interrogation signal's polarity such that the diode is forward biased, a second measurement can be made across the sensor terminals that will generally be different from the first output value since most of the current will pass through the diode. This second output may be correlated with additional predetermined sensor tables to provide additional sensor specific information. As will be appreciated by those skilled in the art, numerous arrangements of electrical componentry are operable to produce different outputs when the componentry is forward biased and when it is reversed-biased. Typically, pluralities of electrical components are required to produce separate output values in response to an interrogation signal applied with two polarities. Further, one of the electrical components will generally be an active component (e.g., components whose response differs in relation to the direction or magnitude of signals presented thereto), such as a diode, in order for the sensor identifying means to produce multiple outputs.

As noted, the processing means will generally be located at a monitor that will receive the outputs generated by the sensor identifying means in the two modes of operation. Additionally, the processor may be operable to measure the response of the sensor identifying means to the application of the interrogation signal in the two modes of operation. For example, in a first mode of operation (e.g., a steady state mode), the processor may take a first measurement of the sensor identifying means' response to the interrogation signal. When the system is switched to the second mode of operation, the processor may measure the sensor identifying means' response to the interrogation signal once or multiple times. If the second mode of operation is a transient mode of operation, the sensor identifying means' response may vary over time such that multiple readings may be taken which define a time/response profile. This time/response profile may, for example, record the variation of the voltage across the sensor identifying means from a first point in time to a second point in time. The monitor may then compare these responses, either singly or in combination, against stored data values and/or profiles. By way of example, the monitor may use the first response/output (e.g., a voltage value) to determine if an interconnected sensor is a sensor or a class of sensors that is recognized by the system (e.g., compare the voltage value to a set of stored voltage values corresponding to a known sensor/class of sensors) and accordingly enable or disable the monitor. The monitor may then use the second response/output (e.g., compare a second voltage reading to a second stored data value) to obtain additional information regarding the sensor (e.g., the particular type of sensor from a class of sensors, calibration data etc.) that may be used to further adjust the operation of the system.

As will be appreciated, since the interrogation signal's polarity is reversed as applied to the sensor identifying means, a single steady state electrical signal may be applied in what amounts to two interrogation signals, one with positive polarity and one with negative polarity, thus allowing for multiple sensor outputs from a steady state signal. Though discussed in reference with a single steady state interrogation signal, it will be appreciated that if more than one interrogation signal is used (e.g., 5 volts and 10 volts) multiple outputs may be obtained for each interrogation signal. Additionally, the system may be operable to generate multiple outputs in response to variable interrogation signals.

In another aspect of the present invention, a method is disclosed to read at least one data value from a photoplethysmographic sensor in a two-mode process. After releasably interconnecting a sensor to a photoplethysmographic monitor wherein the sensor includes first and second sensor terminals and an identifier means electrically coupled between the first and second sensor terminals, a first interrogation signal is applied to the first sensor terminal with an initial polarity to obtain a first output. Then the interrogation signal polarity is reversed such that it is applied to the first sensor terminal with an opposite polarity to obtain a second output. Last, the first and second outputs are employed to identify sensor characteristics to the photoplethysmographic monitor.

The step of reversing may further entail charging an energy storage means with the interrogation signal initial to produce a stored electrical potential and utilizing this stored electrical potential to selectively reverse the interrogation signal's polarity as applied to the first sensor terminal for a predetermined time. The initial interrogation signal may comprise a steady state electrical signal, such as a constant voltage, that may produce a steady state condition across the sensor identifying means. Accordingly, this steady state condition may be measured as a first output reading. Releasing the stored electrical potential on the system may then produce another mode of operation in which the polarity of the interrogation signal is reversed as applied to the first sensor terminal. During this period, at least a second condition, such as a transient response, may be produced across the sensor identifying means; accordingly, a second or multiple measurements may be taken during this period to obtain a second output.

As may be appreciated, employing the first and second outputs may include the sub-steps of first comparing a first data value corresponding with the first output (e.g., a first measured voltage drop) with a first predetermined data range and, second, comparing a second data value corresponding with the second output value (e.g., a second measured voltage drop) with a second predetermined data range. In one arrangement, if either of such comparisons indicate a data value outside of the corresponding predetermined range, the method may further provide for an output to a user (e.g., via a display) indicating that the interconnected sensor is not intended for use with the monitor. Alternatively and/or additionally, the monitor may be automatically disabled for use with the interconnected sensor. Last, when one or more output values are within the predetermined data ranges, the values can be used alone or in combination to select calibration information for use with the sensor.

Additional aspects and corresponding advantages of the present invention will be apparent to those skilled in the art upon consideration of the further description that follows.

DETAILED DESCRIPTION

Figure 1:
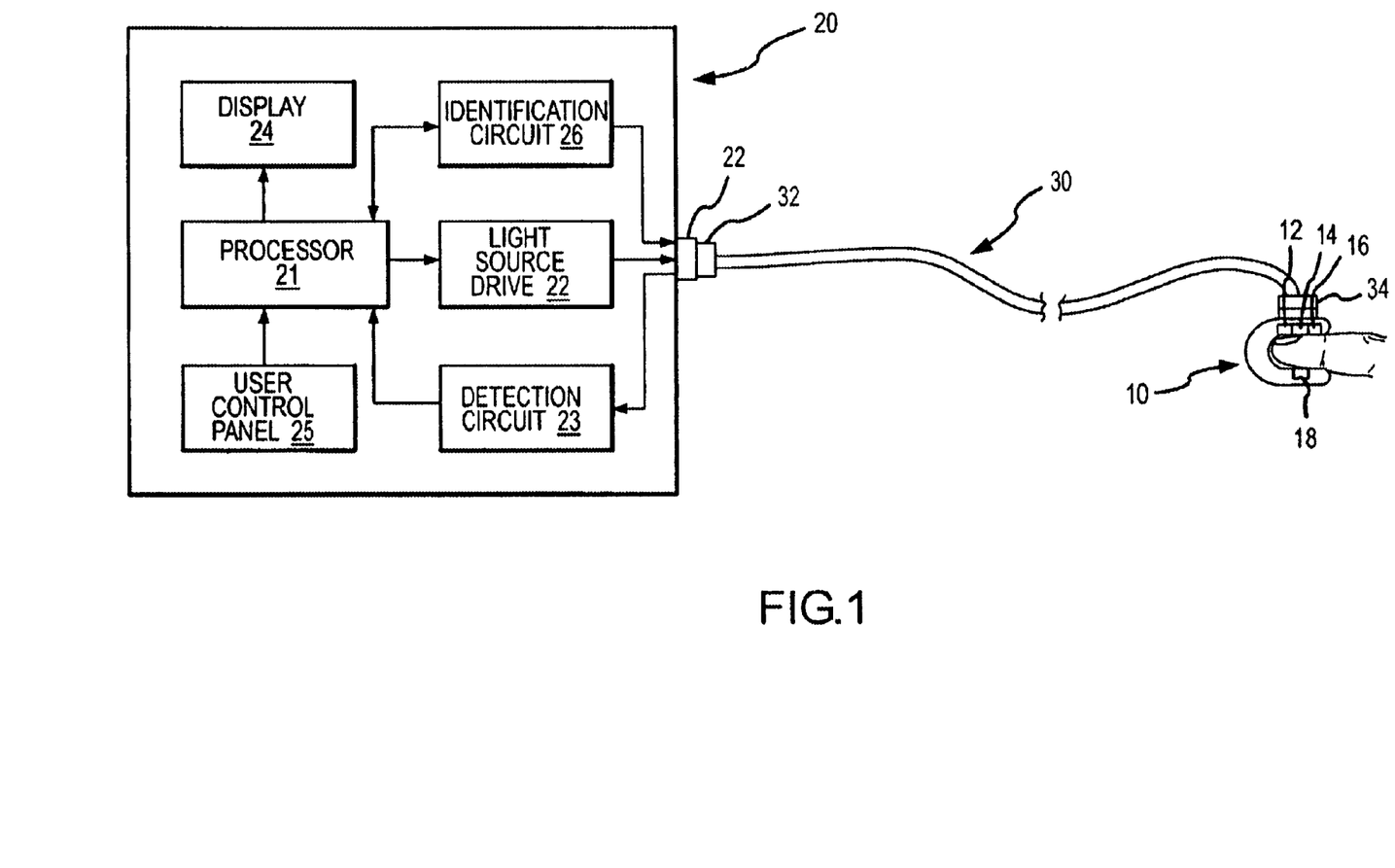
FIG. 1 illustrates a photoplethysmographic system.

FIG. 1 generally illustrates a photoplethysmographic system. In the application of FIG. 1, a photoplethysmographic sensor 10 is interconnected to a photoplethysmographic monitor 20 via a first type of cable 30. As may be appreciated, the photoplethysmographic monitor 20 may vary in type, including differing electrical configurations of its cable interconnection port 22 and corresponding internal processing features. By way of example, monitor 20 may be designed with port 22 including two electrical pins or sockets for driving two light sources for tissue illumination. On the other hand, monitor 20 may be designed with port 22 including three electrical pins or sockets for driving two or more light sources of a photoplethysmographic sensor.

In operation of the system shown in FIG. 1, the photoplethysmographic monitor 20 may comprise a processor 21 that triggers light source drives 22 to transmit drive signals via cable 30 to light sources 12, 14 and/or 16 comprising sensor 10. In turn, sources 12, 14 and/or 16 emit light signals at different, corresponding centered wavelengths. By way of example, in the system application shown in FIG. 1, light sources 12 and 14 may be selectively pulsed to illuminate a patient's tissue under test. Upon tissue illumination, a light detector 18 comprising sensor 10 may detect the intensity of light transmitted by the tissue under test and provide a corresponding output signal.

In applications of the system of FIG. 1, such detector output signal may be transmitted by cable 30 for conversion/conditioning by detection circuit 23 and processing by processor 21 comprising monitor 20. In conjunction with such processing, one or more blood analyte concentration values may be determined and output to a user via monitor display 24. By way of example, the monitor 20 may utilize the detector output signal to determine $SpO_2$ and heart rate values. Monitor 20 may further include a user control panel 25 to allow for user control and override options, as will be further described.

In order for monitor 20 to make accurate determinations regarding analyte concentration values it is important that sensor 10 comprise light sources 12, 14 and/or 16 that emit light at corresponding center wavelengths which are known to monitor 20. For such purposes, sensor 10 is provided with the capability to "identify" itself to monitor 20. As noted above, a sensor may contain an electrical component that has a characteristic that may be measured by a monitor in the identification process. For example, if the sensor's electrical component were a resistor, the monitor may measure this resistance and if this measured resistance corresponds to a known value stored in the monitor, the monitor/sensor combination may be enabled for use. Further, it may desirable to obtain additional sensor information or characteristics once the monitor/sensor combination has been enabled. For example, where the identification means is a resistance value, several separately configured sensors (e.g., infant, nasal septum, finger, etc.) may exist that use the same resistance value, therefore, the sensor may contain a second electrical component such that a second piece of sensor information may be measured to determine which of the sensors in that group is being used. The values measured from the electrical components may be used individually as in the above example or in combination for a number of different purposes such as sensor enablement/disablement, selecting sensor calibration values, and determining individual sensor use characteristics such as hours of use, which may affect a sensor's measurements.

Figure 2:
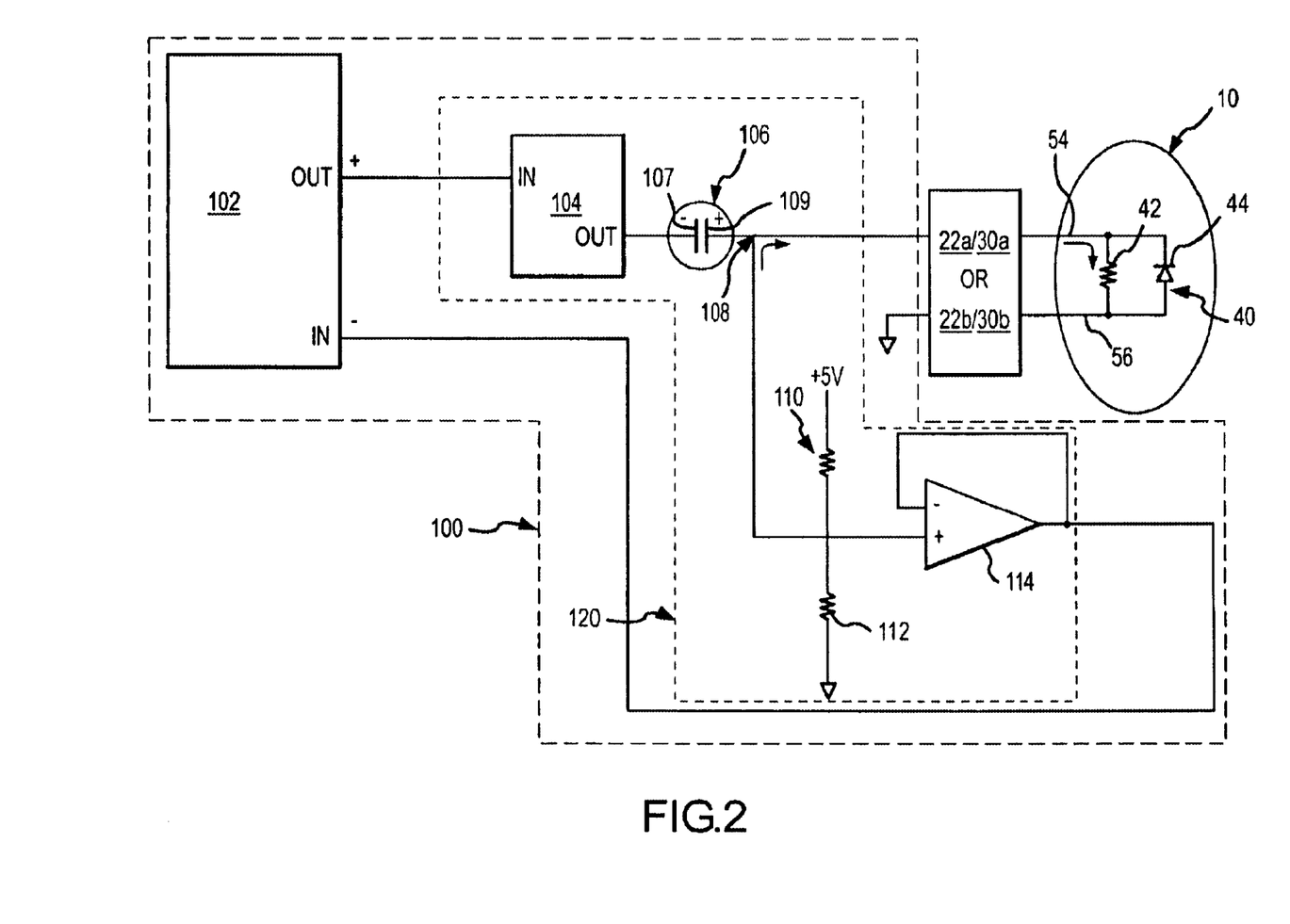
FIG. 2 is an electrical schematic illustration for a two-mode signal generation means in a pulse oximeter monitor employable in the system of FIG. 1.

In this regard, as shown in FIG. 2, sensor 10 comprises an identifier means 40 coupled between first and second sensor terminals 54 and 56, respectively. In the illustrated embodiment, identifier means 40 includes a resistor 42 and a diode 44 interconnected in parallel between the first and second sensor terminals 54 and 56. As will be appreciated, other configurations and additional electrical componentry may be utilized in identifier means 40. However, in all configurations, the electrical componentry will be operable to produce more than one output when a single interrogation signal is applied to the identifier means with opposite polarities. By way of example, an additional identifier resistor (not shown) may be interconnected in series with diode 44 so that both the added resistor and diode 44 are in parallel with resistor 42, allowing the additional resistor to affect the voltage across the sensor terminals when the diode is forward biased.

In order to identify the sensor 10 to monitor 20, processor 21 and identification circuit 26 and procure additional sensor information, the monitor 20 may generate one or more interrogation signals for application to the identifying means 40 included in sensor 10. Identification circuit 26 and processor 21 may obtain one or more corresponding identifying outputs from the identifying means 40 of sensor 10. More particularly, in a first mode, a first interrogation signal with an initial polarity may be applied to sensor terminal 54 wherein the voltage drop across identifying means 40 may be measured. Then, in a second mode, the same interrogation signal may be applied with an opposite polarity to sensor terminal 54 wherein the voltage drop across identifying means 40 may again be measured. In the illustrated embodiment, applying the initial interrogation signal with a positive polarity will cause a voltage drop across the identifying means resistor 42 (i.e., since diode 44 will be reversed-biased and substantially all current will pass through the resistor 42) producing a first output. In the second mode, the diode 44 will be forward-biased and substantially all current will pass therethrough, producing a lower voltage drop across the identifying means 40 and, thus, a second output. As will be appreciated, each output or a combination of both may be compared to predetermined values stored in the monitor 20 to determine pertinent sensor information.

FIG. 2 further shows one embodiment of a signal generating means 100 operable to produce two outputs from a photoplethysmographic sensor 10 using a single interrogation signal. The signal generating means 100 has an establishing means 120 which comprises a power supply 110 (a voltage divider in the illustrated embodiment), an electrical storage means 106 (a capacitor in the illustrated embodiment), and a switching means 104. The signal generating means 100 in the illustrated embodiment also includes a processor 102 interconnected to the switch (e.g., a CMOS gate) 104, which in turn is interconnected to a capacitor 106. Capacitor 106 is interconnectable to sensor 10 (e.g., sensor terminal 54) via monitor port 22 and cable 30. As shown in FIG. 2, capacitor 106 is also interconnected to the voltage divider defined by resistors 110 and 112, as well as to the non-inverting input of buffer amplifier 114. The output of buffer amplifier 114 is interconnected back to microprocessor 102. As shown, sensor identifying means 40 is interconnected in parallel with resistor 112 of the voltage divider.

Figure 3:
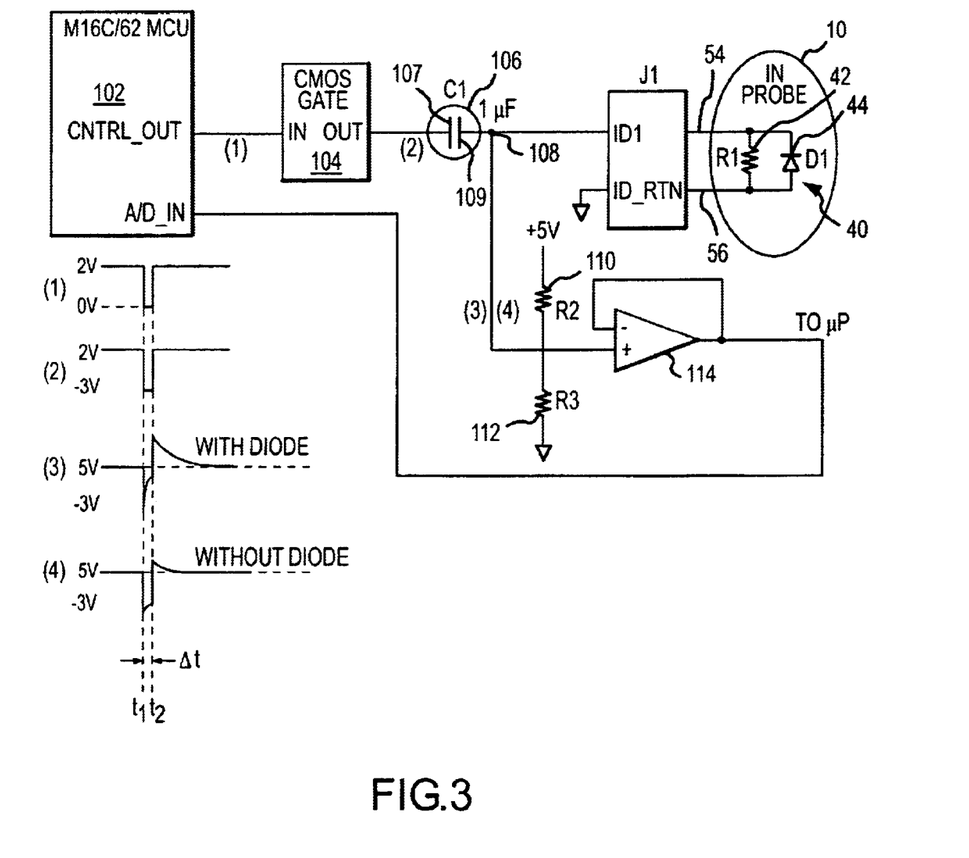
FIG. 3 is an electrical schematic illustration for a two-mode signal generation means, which further details system response at various points.

Operation of the signal generation means 100 (i.e., when sensor 10 is interconnected to monitor 22a) is best understood by reference to FIG. 3 which shows substantially the same circuit as presented in FIG. 2. However, in addition to the signal generation circuit, FIG. 3 shows voltage responses over time for various sites in the system. In particular, response (1) depicts the voltage response over time as measured between microprocessor 102 and switch 104, response (2) depicts the voltage response over time as measured between switch 104 and capacitor 106, and responses (3) and (4) depict the voltage response over time measured at junction 108 for two embodiments of the sensor identifying means. Response (3) depicts the response when identifying means 40 contains a resistor 42 and diode 44 in parallel (as shown). The second response (4), which is shown only for comparative purposes, shows the response if identifying means 40 only contained a resistor 42 between sensor terminals 54 and 56 (not shown). As will be appreciated, the response of junction 108 is the same as the response at terminal 54 and the input of buffer amplifier 114.

In operation of the identifying means containing the diode 44 in parallel with resistor 42, switch 104 may be set so that in a first mode of operation a positive voltage (e.g., 2 volts), provided by microprocessor 104, is seen at the output of switch 104. Additionally, a positive voltage (e.g., 5 volts) as defined by the voltage divider 110 and resistors 42 and 112 may be applied to junction 108 and sensor terminal 54. This same voltage (5 volts) is seen at the input of the buffer amplifier 114 which is converted at the input to processor 102 via an analog-to-digital converter for use by processor 102. As will be appreciated, this results in capacitor 106 having a 5-volt charge on one terminal 107 and a 5-volt charge on a second terminal 109 during steady state operation.

To begin the second mode of operation, the voltage at the output of switch 104 may be switched from a positive voltage (e.g., 2 volts) to ground, at $t_1$, for a predetermined time ($\Delta t$) and then back to a positive voltage (e.g., 2 volts) at $t_2$, via signals provided by microprocessor 102 to switch 104. This selective grounding of the signal generating means 100 at $t_1$ causes the discharge of the capacitor 106; however, as will be appreciated, there cannot be an instantaneous change of voltage across the terminals of a capacitor. Therefore, at $t_1$ the output of the processor 102, as shown by response (1), drops from the initial voltage (2 volts) to zero and sections (2) and (3) are pulled negative by −3 volts, the difference in potential across the capacitor. Accordingly, circuit junction 108 and sensor terminal 54 are pulled to a negative voltage. Responses (2) and (3) show the corresponding drop in voltage of the sections (2) and (3) at $t_1$. Junction 108 will return to a steady state positive voltage as capacitor 106, which still contains a charge at terminal 109, is discharged through the parallel impedance of resistors 110, 112, and identifying means 40. In the latter regard, when a negative charge is applied to sensor terminal 54 current flow through identifying means 40 is reversed. As shown by response (3), upon initially switching to the second mode of operation the voltage in section (3) drops to −3 volts. During the time section (2) remains grounded ($\Delta t$), the potential stored on the capacitor terminal 109 will discharge across capacitor 106 to capacitor terminal 107 and to ground. The rate of discharge will be affected by the parallel impedance of resistors 110, 112 and identifying means. When a diode is present in the identifying means and forward-biased the rate of discharge will be greatly increased, as shown by the sharp upward slope of the voltage in response (3) over $\Delta t$. In comparison, response (4) shows a much slower discharge when only a resistor is present in identifying means 40. As will be appreciated, the system would return to a steady state mode of operation if the capacitor were allowed to fully discharge.

At the second switch at $t_2$ (i.e., positive going), sections (1) and (2) are returned to 2 volts and the voltage at the voltage divider will be pulled positive (e.g., 5 volts), resulting in a positive voltage being restored at junction 108. In addition, there will be a voltage overshoot equal to the discharge of the capacitor in section (3). This voltage overshoot will discharge through RC time constants until a steady state voltage (e.g., 5 volts) is restored. During the above process, the voltage at junction 108 may be sampled through the buffer amplifier 114 by the analog and digital converter at the input of processor 102 once or continuously, and thereby provide a second measurement or a time profile of the interrogation signal as seen through the identifying means during the second mode of operation.

Again referring to FIG. 2, the identifying means 40 can utilize numerous combinations of electrical components between the sensor terminals 54, 56. However, as noted above, the components are combined so as to provide different outputs when positive and negative polarities are applied across the sensor terminals 54 and 56. In the illustrated embodiment, when a positive voltage is applied to terminal 54, diode 44 is reverse-biased so that substantially all current flowing through information circuit 40 passes through resistor 42, thereby lowering the voltage seen at the non-inverting input of the buffer amplifier 114. In turn, the observed voltage at buffer 114 is converted at the input to microprocessor 102 via an analog-to-digit converter for use by processor 102 to identify sensor 10 characteristics (e.g., via comparison of the voltage value to a predetermined range associated with a compatible sensor). When a negative voltage is applied to terminal 54, the current discharging the capacitor 106 bypasses the resistor 42 and flows through the diode 44. In turn, a second voltage is observed at buffer 114 and converted by the processor 102 to identify additional sensor 10 characteristics. The voltage seen at junction 108 after either switch or over a period of time may be compared to a predetermined value range, e.g., corresponding with the voltage that should be seen when diode 44 is present in the interconnected sensor. Such comparison can be realized to confirm the compatibility of the interconnected sensor 10 with a monitor 20 and/or can otherwise be utilized for calibration purposes in blood analyte concentration determinations. The signal generation means 120 provides a simple apparatus wherein one input signal can be applied to a sensor terminal with two polarities to produce two separate outputs from the sensor.

Figure 4:
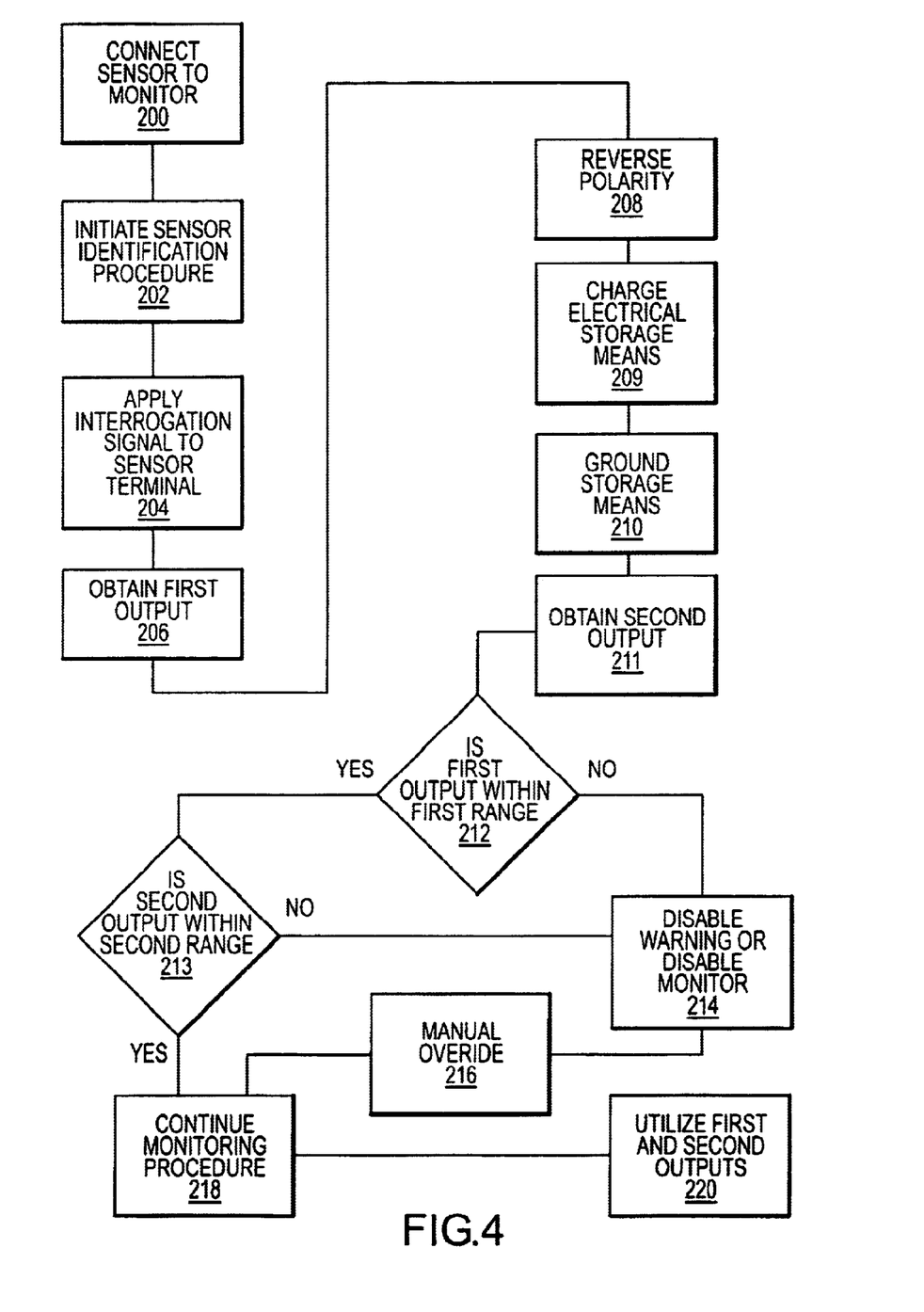
FIG. 4 is a flow diagram of one process embodiment of the present invention.

The photoplethysmographic monitor 20 may be provided with pre-programmed or preset process functions to utilize the outputs from the identifying means. Referring to FIG. 4, following interconnection 200 of sensor 10 to monitor 20, a sensor information procedure may be initiated (step 202). Such sensor information procedure may be automatically initiated by monitor 20 upon electrical sensing of one or more of the interconnections made in step 200 above. Alternatively, the sensor information procedure may be initiated by a user via interface with user control panel 25 of monitor 20, e.g., upon prompting by display 24 of monitor 20. In any case, monitor 20 may be pre-programmed so that the sensor information procedure must be completed or manually overridden by a user before photoplethysmographic patient monitoring of blood analyte concentration, etc. can proceed.

Upon initiation of the sensor information procedures, monitor 20 may automatically apply a first interrogation signal to a first sensor terminal (step 204) and correspondingly obtain a first output value (206). The interrogation signal polarity may then be reversed by monitor 20 to the first sensor terminal (step 208). Reversing signal polarity may further comprise the sub-steps of charging an electrical storage means (step 209) using the first interrogation signal such that there is a stored electrical potential in the system. The second sub-step of reversing includes selectively grounding (step 210) the stored electrical potential in the signal generation means 120 to reverse the interrogation signal polarity for a predetermined time. Correspondingly, a second output value may be obtained at the first sensor terminal (step 211).

Upon obtainment of the output values, processor 21 of monitor 20 may determine whether the value extracted from the first output is within a first predetermined range (step 212). By way of example, in the arrangement shown in FIG. 2 a voltage output value from buffer amplifier 114 may be compared with a predetermined voltage range wherein a value within the range indicates that a known, compatible sensor (i.e., sensor 10) is interconnected to the monitor 20. Next, the processor 21 of monitor 20 may determine if the second output is within a second predetermined range (step 213). If both outputs are within their respective predetermined ranges, the processor 21 may automatically provide for continuation of photoplethysmographic monitoring procedure (step 218), wherein one or more blood analyte concentration levels are determined by sensor 10 and the monitor 20. Alternatively, processor 21 may provide an output to a user (e.g., at display 24) indicating that a compatible sensor (i.e., sensor 10) has been detected and prompt the user to provide an input at user control panel 25 to initiate photoplethysmographic monitoring procedures. In conjunction with blood analyte concentration determinations, the first information output value may be utilized to select appropriate calibration values for sensor 10 (step 220).

In the event that the first, second or both information output values are outside of the corresponding predetermined range, processor 21 may be pre-programmed to disable monitor 20 from continuing a photoplethysmographic monitoring procedure (step 214). Such disablement may be accompanied by a corresponding output at display 24, indicating to the user that an inappropriate or incompatible sensor has been interconnected to the monitor 20. Alternatively, a warning signal may be output to a user at display 24, whereupon processor 21 may be pre-programmed to allow a user to provide an override input at the user control panel 25 and continue photoplethysmographic monitoring procedures (step 216).

The embodiment described above is for exemplary purposes only and is not intended to limit the scope of the present invention. Various adaptations, modifications and extensions of the described sensor/system/method will be apparent to those skilled in the art and are intended to be within the scope of the invention as defined by the claims that follow.

What is claimed is:

1. A photoplethysmographic system for use in determining at least one data value corresponding with a photoplethysmographic sensor comprising:

signal generation means for generating at least one interrogation signal in each of a first mode of operation and a second mode of operation;

sensor identifying means for receiving said at least one interrogation signal, wherein a first polarity is established at a first sensor terminal throughout said first mode of operation and an opposite second polarity is established at the first terminal throughout said second mode of operation, and wherein said identifying means produces a first output in said first mode of operation and a second output in said second mode of operation; and processor means for employing said first and second outputs to determine at least a first data value corresponding with said sensor.

2. A photoplethysmographic system as recited in claim 1, wherein said signal generation means comprises means for establishing said first and second modes of operation.

3. A photoplethysmographic system as recited in claim 2, wherein said means for establishing comprises:

a power supply for providing at least one said interrogation signal having said first polarity at said first terminal;

an electrical storage means for storing an electrical potential from said power supply; and a switching means for selectively discharging said electrical storage means to produce said opposite second polarity at said first terminal.

4. A photoplethysmographic system as recited in claim 3, wherein said power supply comprises a steady state power source.

5. A photoplethysmographic system as recited in claim 4, wherein said steady state power source comprises a voltage divider for providing said constant voltage.

6. A photoplethysmographic system as recited in claim 3, wherein said electrical potential has an equal voltage and opposite polarity of said power supply.

7. A photoplethysmographic system as recited in claim 6, wherein said electrical storage means comprises a capacitor.

8. A photoplethysmographic system as recited in claim 3, wherein said switching means is selectively activable to change said system from said first mode of operation to said second mode of operation for a predetermined time.

9. A photoplethysmographic system as recited in claim 8, further comprising a processing means for selectively activating said switching means.

10. A photoplethysmographic system as recited in claim 2, wherein said signal generating means is located at least partially in a cable connecting said photoplethysmographic sensor to said processing means.

11. A photoplethysmographic system as recited in claim 2, wherein said signal generating means is located at least partially in said photoplethysmographic sensor.

12. A photoplethysmographic system as recited in claim 2, wherein said signal generating means is located at least partially in a photoplethysmographic monitor.

13. A photoplethysmographic system as recited in claim 1, wherein said identifying means comprises a plurality of electrical components electrically interconnected between said first sensor terminal and second sensor terminals.

14. A photoplethysmographic system as recited in claim 13, wherein at least one of said plurality of electrical components is an active component.

15. A photoplethysmographic system as recited in claim 1, wherein said first output comprises at least a first response to said interrogation signal as established at said first terminal in said first mode of operation.

16. A photoplethysmographic system as recited in claim 15, wherein said first mode of operation comprises a steady state mode of operation.

17. A photoplethysmographic system as recited in claim 15, wherein said second mode of operation comprises a transient mode of operation.

18. A photoplethysmographic system as recited in claim 1, wherein said second output comprises at least a first response to said interrogation signal as established at said first terminal in said second mode of operation.

19. A photoplethysmographic system as recited in claim 18, wherein said second mode of operation takes place over a predetermined time and said second output comprises a plurality of said responses over said predetermined time.

20. A photoplethysmographic system as recited in claim 19, wherein said second output comprises a time profile of said plurality of said responses over said predetermined time.

21. A photoplethysmographic system as recited in claim 18, wherein said second mode of operation comprises a transient mode of operation.

22. A photoplethysmographic system as recited in claim 1, wherein said processing means is operable to compare said first and second outputs to stored data values to determine data particular to said sensor.

23. A photoplethysmographic system as recited in claim 1, wherein said processing means comprises a photoplethysmographic monitor.

24. The photoplethysmographic system as recited in claim 1, wherein said first and second outputs are different.

25. The photoplethysmographic system as recited in claim 1, wherein a positive voltage is established at said first terminal throughout one of said first and second modes and a negative voltage is established at said first terminal throughout the other of said first and second modes.

26. The photoplethysmographic system as recited in claim 25, wherein at least one of said positive and negative voltages comprises a transient voltage during at least a portion of the respective said mode.

27. The photoplethysmographic system as recited in claim 1, wherein said interrogation signal establishes a current flow in a first direction relative to said first sensor terminal throughout said first mode and wherein said interrogation signal establishes a current flow in a second direction relative to said first sensor terminal throughout said second mode.

28. The photoplethysmographic system as recited in claim 27, wherein a magnitude of said current flow is transient during at least a portion of one of said first and second modes.

29. The photoplethysmographic system as recited in claim 1, wherein said sensor identifying means is interconnected between said first sensor terminal and a second sensor terminal.

30. The photoplethysmographic system as recited in claim 29, wherein said processor means is operative to identify changes in said at least one interrogation signal as applied across said first and second terminals in said first and second modes of operation.

31. The photoplethysmographic system as recited in claim 29, wherein at least one of said first and second outputs comprises a voltage drop between said first and second terminals.

32. The photoplethysmographic system as recited in claim 31, wherein the other of said first and second outputs is substantially the same as said at least one interrogation signal.

33. A method to determine at least one data value from a photoplethysmographic sensor comprising the steps of:
    applying an interrogation signal having a first polarity throughout a first mode of operation to a photoplethysmographic sensor with an identifying means between at least a first and second terminal, wherein a first output is obtained in said first mode of operation;
    reversing the polarity of said interrogation signal to apply an opposite second polarity to said photoplethysmographic sensor identification means throughout a second mode of operation, wherein a second output is obtained in said second mode of operation; and
    employing said first and second outputs to determine at least one data value corresponding with said photoplethysmographic sensor.

34. The method of claim 33, wherein said step of applying an interrogation signal comprises applying a steady state electrical signal to said identifying means.

35. The method of claim 33, wherein obtaining said first output comprises measuring a steady state response of said interrogation signal as applied to said identifying means.

36. The method of claim 33, wherein said step of reversing further comprises:
    supplying an interrogation signal with said first polarity to said first terminal;
    charging an energy storage means with said interrogation signal to store an electrical potential; and
    utilizing said electrical potential to selectively reverse said interrogation signal polarity as applied to said first terminal for a predetermined time to establish said second opposite polarity, wherein at least one said second output is obtained during said predetermined time.

37. The method of claim 36, wherein obtaining said second output comprises measuring a transient response of said interrogation signal as applied to said identifying means during said predetermined time.

38. The method of claim 37, wherein measuring said transient response comprises taking a plurality of measurements during said predetermined time.

39. A method as recited in claim 33, said employing step comprising:
    comparing at least one of first and second outputs with at least a first predetermined data range.

40. A method as recited in claim 33, wherein when at least one of said first and second outputs is outside of a first and second predetermined data range, respectively, said method further comprises at least one of the following steps:
    providing an output signal to a user to indicate that the photoplethysmographic sensor is outside at least one of said first and second predetermined data ranges; and,
    disabling the photoplethysmographic monitor for use with the interconnected photoplethysmographic sensor.

41. A method as recited in claim 40, further comprising:

displaying a visual message to a user at said photoplethysmographic monitor indicating one of:
that at least one of said first and second outputs associated with said photoplethysmographpic sensor is outside of at least one of said first and second predetermined data ranges; and
that said photoplethysmographic monitor is disabled.

42. A method as recited in claim 33, wherein when said first output is within a first predetermined data range and said second output is within said second predetermined data range, said method further comprises:

utilizing said photoplethysmographic sensor to obtain an identification signal indicative of light absorption by the tissue-under-test; and, employing said detector signal to obtain a concentration value for at least one blood analyte.

43. A method as recited in claim 33, said employing step including:

utilizing at least one of said first output and second output to select one of a plurality of a calibration values for use with said sensor.

44. The method of claim 33, wherein obtaining said outputs comprises obtaining first and second outputs wherein said outputs are different.

45. The method of claim 33, wherein obtaining said first and second outputs each comprises measuring a change in said interrogation signal across said first and second terminals.

46. The method of claim 45, wherein measuring a change comprises measuring a voltage change across said first and second terminals for at least one of said first and second outputs.

47. A photoplethysmographic system for use in determining at least one data value corresponding with a photoplethysmographic sensor comprising:

signal generation means for generating at least one interrogation signal in each of a first mode of operation and a second mode of operation;

sensor identifying means for receiving said at least one interrogation signal across first and second terminals in each of said first and second modes of operation, said sensor identifying means being operable to produce first and second outputs in said first and second modes of operation, respectively, wherein one of said first and second outputs is substantially the same as said at least one interrogation signal; and processor means for employing said first and second outputs to determine at least a first data value corresponding with said sensor.

48. The photoplethysmographic system as recited in claim 47, wherein said signal generation means establishes a first polarity across said first and second terminals in said first mode of operation and establishes an opposite second polarity across said first and second terminals in said second mode of operation.

49. The photoplethysmographic system as recited in claim 48, wherein said first polarity is maintained throughout said first mode of operation and said opposite second polarity is maintained throughout said second mode of operation.

50. The photoplethysmographic system as recited in claim 47, wherein said sensor identifying means comprises parallel electrical paths between said first and second terminals.

51. The photoplethysmographic system as recited in claim 50, wherein one of said parallel electrical paths contains a unidirectional electrical component.

52. The photoplethysmographic system as recited in claim 51, wherein said unidirectional electrical component comprises a diode.

53. The photoplethysmographic system as recited in claim 51, wherein the other of said parallel electrical paths comprises an electrical component operable to produce a voltage drop in response to axis applied signal between said first and second terminals.

54. The photoplethysmographic system as recited in claim 51, wherein said processing means is further operative to compare at least one of said first and second outputs with at least a first set of predetermined data values.

55. The photoplethysmographic system as recited in claim 54, wherein upon determining at least one of said first and second output is outside of at least one range of said predetermined data values, said processor being further operative to:

provide an output signal to a user to indicate that the photoplethysmographic sensor is outside said range of predetermined data values; and, disable the photoplethysmographic monitor for use with the interconnected photoplethysmographic sensor.

* * * * *

UNITED STATES PATENT AND TRADEMARK OFFICE
CERTIFICATE OF CORRECTION

PATENT NO. : 6,668,183 B2  Page 1 of 1
DATED : December 23, 2003
INVENTOR(S) : Hicks et al.

It is certified that error appears in the above-identified patent and that said Letters Patent is hereby corrected as shown below:

Column 11,
Line 7, delete the word "terminals", and insert therefor -- terminal --.

Column 13,
Line 5, delete the word "photoplethysmographpic", and insert therefor -- photoplethysmographic --.

Column 14,
Line 28, delete the word "axis", and insert therefor -- an --.

Signed and Sealed this

Twenty-fourth Day of February, 2004

JON W. DUDAS
*Acting Director of the United States Patent and Trademark Office*